(12) United States Patent
Ashby (10) Patent No.: US 10,136,842 B2
(45) Date of Patent: Nov. 27, 2018

(54) FOOTWEAR APPARATUS WITH TECHNIQUE FEEDBACK

(71) Applicant: ICON Health & Fitness, Inc., Logan, UT (US)

(72) Inventor: Darren C. Ashby, Richmond, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 345 days.

(21) Appl. No.: 14/944,944

(22) Filed: Nov. 18, 2015

(65) Prior Publication Data

US 2016/0143562 A1   May 26, 2016

Related U.S. Application Data

(60) Provisional application No. 62/085,197, filed on Nov. 26, 2014.

(51) Int. Cl.
*A61B 5/00* (2006.01)
*A61B 5/11* (2006.01)
*A43B 3/00* (2006.01)
*A61B 5/103* (2006.01)

(52) U.S. Cl.
CPC ............ *A61B 5/112* (2013.01); *A43B 3/001* (2013.01); *A61B 5/1038* (2013.01); *A61B 5/486* (2013.01); *A61B 5/6807* (2013.01); *A61B 5/742* (2013.01); *A61B 5/7455* (2013.01); *A61B 2503/10* (2013.01)

(58) Field of Classification Search
CPC ......... A61B 5/11; A61B 5/112; A61B 5/1123; A61B 5/1036; A61B 5/1038
See application file for complete search history.

(56) References Cited

U.S. PATENT DOCUMENTS

| | | | |
|---|---|---|---|
| 5,408,873 A | 4/1995 | Schmidt et al. | |
| 6,978,684 B2 * | 12/2005 | Nurse | A61H 3/00 73/862.041 |
| 7,292,151 B2 | 11/2007 | Ferguson et al. | |
| 9,427,179 B2 * | 8/2016 | Mestrovic | A61B 5/01 |
| 9,446,287 B2 * | 9/2016 | Weast | A61B 5/112 |
| 9,504,290 B2 * | 11/2016 | Andoh | A43B 3/0005 |
| 9,504,407 B2 * | 11/2016 | Lam | A61B 5/112 |
| 2003/0120353 A1 | 6/2003 | Christensen | |
| 2006/0085047 A1 | 4/2006 | Unsworth et al. | |
| 2008/0287832 A1 | 11/2008 | Collins et al. | |
| 2011/0098605 A1 | 4/2011 | deGreef et al. | |

* cited by examiner

*Primary Examiner* — Max Hindenburg
(74) *Attorney, Agent, or Firm* — Ray Quinney & Nebeker (57) ABSTRACT

A footwear apparatus includes a sensor in the footwear apparatus positioned to monitor an activity technique of the user when the footwear apparatus is joined with a foot of the user and a feedback generator is arranged to produce at least one of a haptic communication or an optical communication to the user in response to detecting a pattern in the activity technique.

20 Claims, 5 Drawing Sheets

FOOTWEAR APPARATUS WITH TECHNIQUE FEEDBACK

RELATED APPLICATIONS

This application claims priority to U.S. patent application Ser. No. 62/085,197 titled "Footwear Apparatus with Technique Feedback" and filed on 26 Nov. 2014, which application is herein incorporated by reference for all that it discloses.

BACKGROUND

Running is a popular form of aerobic exercise that many perform to stay fit. Good running technique can help runners avoid injury, run faster, and conserve energy. Good running technique involves having good posture, good stride length, an optimal stride frequency and relaxed upper body. Good form also includes avoiding heel striking heel by the runner. Such techniques often take practice to master as the techniques may not be the runner's natural inclination.

One mechanism for monitoring a user's technique is disclosed in U.S. Pat. No. 8,280,681 issued to Curtis A. Vock, et al. In this reference, a system of monitoring weight of a person includes a plurality of pressure sensors integrated with a shoe, for generating wireless signals responsive to weight of a person wearing the shoe when walking or running over ground. A processor processes the signals to determine an improper walking or running event, and a transmitter transmits a signal indicative of the improper walking or running event. A remote receiver receives the signal and generates an indication of the improper walking or running event. Other types of mechanisms for monitoring a user's technique are described in U.S. Patent Application No. 2008/0066343 issued to Lillian Sanabria-hernandez and U.S. Pat. No. 6,356,856 issued to Erik P. N. Damen, et al. All of these references are herein incorporated by reference for all that they disclose.

SUMMARY

In one aspect of the invention, a footwear apparatus includes a sensor in the footwear apparatus positioned to monitor an activity technique of the user when the footwear apparatus is joined with a foot of the user.

In one aspect of the invention, the footwear apparatus includes a feedback generator arranged to produce at least one of a haptic communication or an optical communication to the user in response to detecting a pattern in the activity technique.

In one aspect of the invention, the pattern is undesirable for the activity technique.

In one aspect of the invention, the footwear apparatus comprises a shoe.

In one aspect of the invention, the haptic communication includes an electric shock.

In one aspect of the invention, the haptic communication includes a mechanical mechanism arranged to come into contact with the foot.

In one aspect of the invention, the optical communication includes illuminating a light emitting diode.

In one aspect of the invention, the feedback generator comprises an actuator capable of moving an impingement head into contact with the foot.

In one aspect of the invention, the impingement head is one of multiple impingement heads.

In one aspect of the invention, the impingement heads are distributed throughout a support member of the footwear apparatus in a heel region of the support member, a toe region of the support member, a mid-foot region of the support member or combinations thereof.

In one aspect of the invention, the impingement head is connected to an impingement body at least partially submerged in a thickness of a support member of the footwear apparatus.

In one aspect of the invention, the impingement head is positioned such that the foot lands on the impingement head when the impingement head is caused to protrude beyond foot engagement surface of the support member.

In one aspect of the invention, the pattern includes a toe striking element.

In one aspect of the invention, the pattern includes a heel striking element.

In one aspect of the invention, the pattern includes a mid-foot striking element.

In one aspect of the invention, the pattern includes a pronation element.

In one aspect of the invention, a footwear apparatus includes a sensor in the footwear apparatus positioned to monitor an activity technique of the user when the footwear apparatus is joined with a foot of the user.

In one aspect of the invention, the footwear apparatus includes a feedback generator arranged to produce a haptic communication to the user in response to detecting an undesirable pattern in the activity technique.

In one aspect of the invention, the footwear apparatus includes the haptic communication includes a mechanical mechanism arranged to come into contact with the foot.

In one aspect of the invention, the haptic communication is executed with impingement heads.

In one aspect of the invention, the impingement heads are distributed throughout a support member of the footwear apparatus in a heel region of the support member, a toe region of the support member, a mid-foot region of the support member or combinations thereof.

In one aspect of the invention, the impingement head is connected to an impingement body at least partially submerged in a thickness of a support member of the footwear apparatus.

In one aspect of the invention, the footwear apparatus includes a sensor in the footwear apparatus positioned to monitor an activity technique of the user when the footwear apparatus is joined with a foot of the user.

In one aspect of the invention, the footwear apparatus includes a feedback generator arranged to produce a haptic communication to the user in response to detecting an undesirable pattern in the activity technique.

In one aspect of the invention, the footwear apparatus includes the haptic communication includes a mechanical mechanism arranged to come into contact with the foot.

In one aspect of the invention, the footwear apparatus includes the impingement head is one of multiple impingement heads.

In one aspect of the invention, the footwear apparatus includes the impingement heads are distributed throughout a support member of the footwear apparatus in a heel region of the support member, a toe region of the support member, a mid-foot region of the support member or combinations thereof.

In one aspect of the invention, the footwear apparatus includes the impingement head is connected to an impingement body at least partially submerged in a thickness of a support member of the footwear apparatus.

In one aspect of the invention, the footwear apparatus includes the impingement head is positioned such that the foot lands on the impingement head when the impingement head is caused to protrude beyond foot engagement surface of the support member.

Any of the aspects of the invention detailed above may be combined with any other aspect of the invention detailed herein.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

Running form can be affected by multiple factors. For example, stride length and stride frequency determine the runner's speed. However, a user will often attempt to increase his or her speed by increasing his or her stride length while decreasing his or her stride frequency, which may not actually increase the runner's speed. Also, some runners tend to strike the ground with their heel first and pivot their foot forward during a step. Such a heel strike can cause injury and is inefficient. Also, running with a forward lean can be beneficial because such a lean can help the runner avoid bouncing up and down as the runner propels himself or herself forward.

Figure 1:
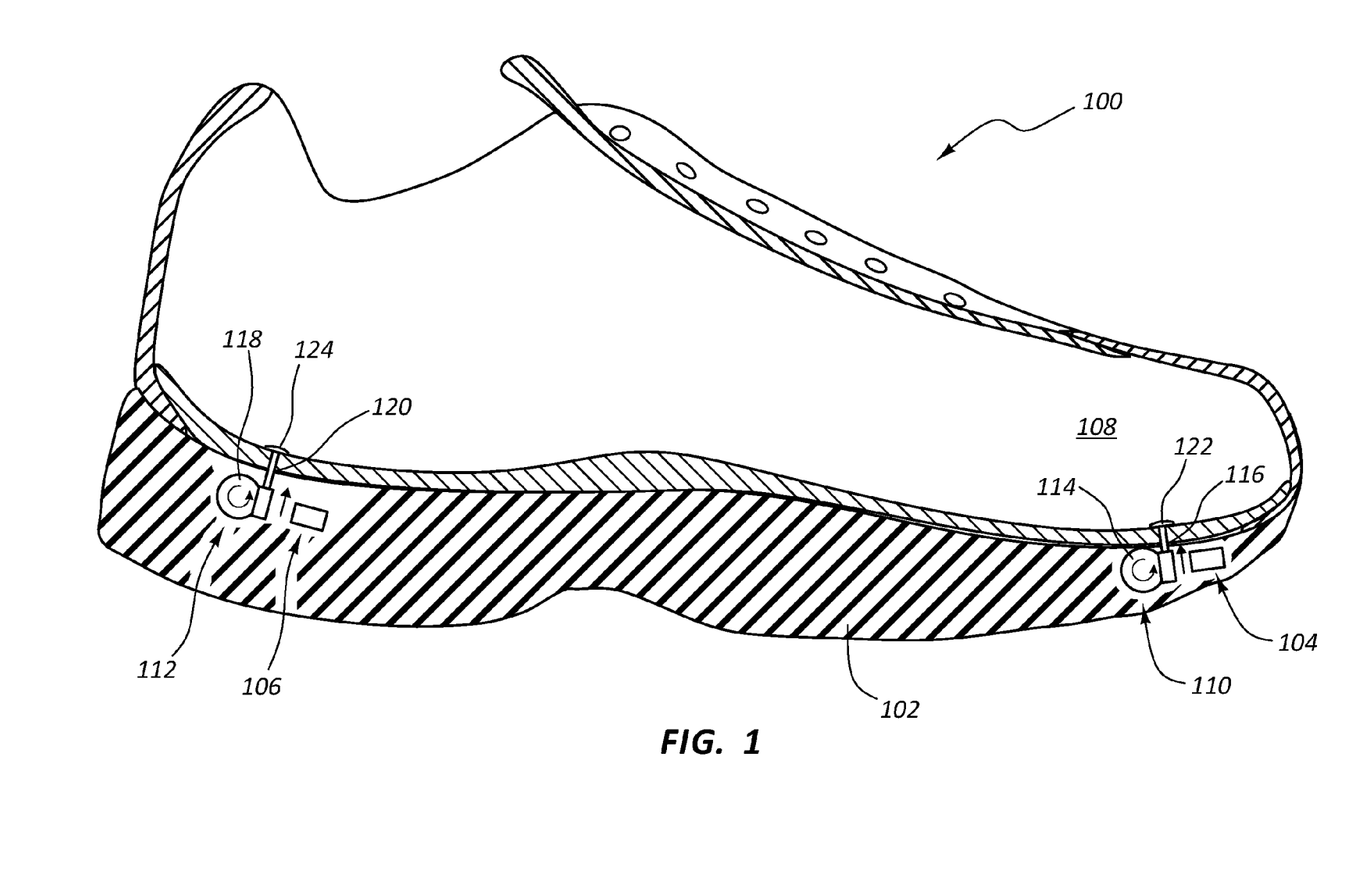
FIG. 1 illustrates a cross sectional view of an example of a footwear apparatus in accordance with the present disclosure.
Figure 2:
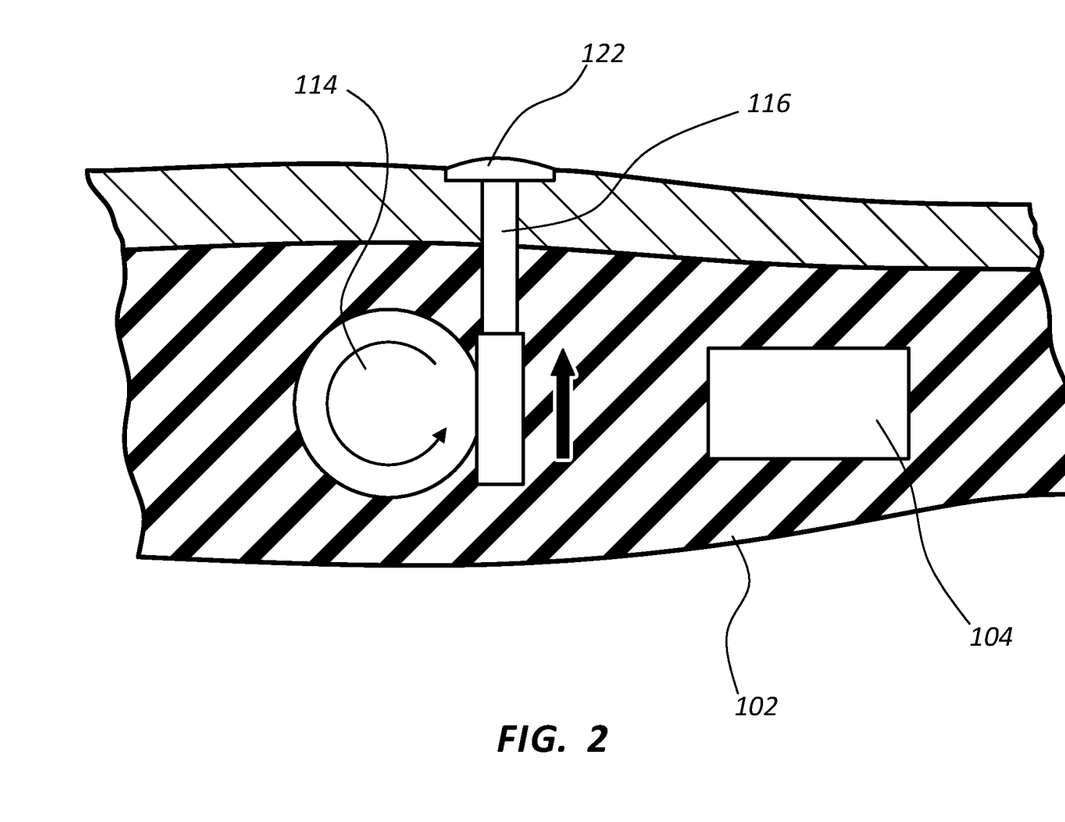
FIG. 2 illustrates a cross sectional view of an example of a feedback generator in accordance with the present disclosure.

Particularly, with reference to the figures, FIGS. 1-2 include an example of a footwear apparatus 100 in accordance with the present disclosure. In this example, the footwear apparatus is a running shoe that includes a support member, such as a sole 102 of the shoe. On a front side of the shoe, a front sensor 104 is located in the sole 102. Likewise, on a rear side of the shoe, a rear sensor 106 is located in the sole 102. While this embodiment will be described with reference to just a front sensor 104 and a rear sensor 106 disposed within a sole 102 of a footwear apparatus 100, other sensors may be positioned at other locations of a footwear apparatus. For example, the sensors may be positioned on a right side of the shoe, a left side of the shoe, a mid-section of the shoe, another section of the shoe or combinations thereof. Further, the sensors may or may not be located within the sole 102. For example, the sensors may be located above the sole 102, on an outside of the shoe, on an underside of the sole 102, within a top side of a cavity 108 in which the foot is disposed, elsewhere inside of the cavity 108 or combinations thereof. Additionally, any appropriate number of sensors may be used in accordance with the present invention. While the illustrated example depicts two sensors, other examples may include one sensor, three sensors, up to twenty sensors, up to a hundred sensors, another number of sensors or combinations thereof.

The front sensor 104 and the rear sensor 106 may detect impacts, movements or other characteristics associated with walking, running, dancing, another sport, another activity or combinations thereof. For example, at least one of the front and rear sensors 104, 106 may be a pressure sensor that is constructed to detect a varying load during such activities performed by the user. As a user's weight is positioned over either the front or the rear sensors 104, 106, the sensor may detect an increased amount of pressure. Similarly, as the user's weight is shifted off of the sensor, the sensor may detect a decreased amount of pressure. The readings of the front sensor 104 and the rear sensor 106 may be sent to a processor for interpretation. For example, the processor may make a determination that the user is striking his or her heel on the ground in response to a pressure reading from the rear sensor 106 that exceeds a predetermined pressure threshold. In another example, a reading from the front sensor 104 that indicates an increased pressure may be interpreted to be that the user is pushing off with his or her toes. However, the amount of pressure, the direction of magnitude of pressure, the patterns of pressure loads and/or amounts, other characteristics or combinations thereof may be analyzed to determine other foot positions or events occurring in the user's activity. Such positions and events can be used to determine the user's technique for the activity that the user is performing. For example, the readings of the sensors 104, 106 may be used to determine that the user is striking his or her heel against the ground as he or she runs. In other circumstances, the readings of the sensors 104, 106 may be used to determine the user's stride length and stride frequency based on the number of times it appears that the shoe is making contact with the ground. While these examples have been described with reference to just certain types of events occurring during the activity, the sensors may be used to determine any appropriate type of event for any appropriate type of activity.

In some cases, other sensors may be used to help determine the types of events. For example, a global positioning system or another type of location device may be used in conjunction with the front and rear sensors 104, 106 to determine the stride length and/or stride frequency.

In some examples, at least one of the front and rear sensors 104, 106 is an accelerometer. The accelerometer may be used to measure the movements of the footwear apparatus. Such measurements may identify when there are changes in the direction that the footwear apparatus is moving, which may indicate that the user is transitioning from a first step to a second step or some other event is occurring. Further, accelerometer measurements may be used to determine which part of the footwear is contacting the ground relative to other parts. For example, the accelerometer measurements may be able to identify the time lag between when the rear portion of a shoe contacts the ground and a front portion of the shoe contacts the ground.

The footwear apparatus may also include at least one feedback generator. In the illustrated example, the shoe includes a front feedback generator 110 partially submerged within the front portion of the sole 102 and a rear feedback generator 112 partially submerged within the rear portion of the sole 102. The feedback generators 110, 112 may include mechanisms to provide feedback to the user when the user executes poor technique associated with the activity being performed by the user. For example, if the user is running and the user's running technique is bad, the feedback generators 110, 112 can provide an appropriate stimulus to the user to indicate that the technique is bad and to motivate the user to improve the technique.

In some examples, the motivation to improve the technique is generated at least in part by the type of stimulus provided. Such a stimulus may cause at least some discomfort to the user, thereby causing the user have a desire to change how he or she is running. Further, the location of where the stimulus is provided may also cause the user to desire to change his or her technique. Continuing with the examples where the activity is running, the rear feedback generator 112 may cause a stimulus with at least some level of discomfort to be applied to the rear of the user's foot when the user's running technique includes heel striking. Such discomfort at the user's heel may motivate the user to adjust his or her running technique to avoid striking his or her heel.

The front feedback generator 110 may include a front actuator 114 and a front pin 116, and the rear feedback generator 112 may include a rear actuator 118 and a rear pin 120. A front impingement head 122 may be connected to the front pin 116, and a rear impingement head 124 may be connected to the rear pin 120. The front and rear actuators 114, 118 may cause the front and rear pins 116, 120 to move towards the user's foot. As a result, the front and rear impingement heads 122, 124 may contact the user's foot. In some examples, the impingement heads 122, 124 have a geometry that causes discomfort to the user when the impingement heads 122, 124 contact the foot. In some cases, both of the front and rear feedback generators 110, 112 are activated at the same time. In other cases, just a subset of all of the feedback generators are selectively activated to motivate the user to correct his or her technique in specific ways. While the examples above have been described with reference to just a front feedback generator and a rear feedback generator, any appropriate number of feedback generators may be used in accordance with the present invention. Further, while the feedback generators are shown partially disposed within the sole of a shoe, the feedback generators may be located at any appropriate location of the footwear apparatus. For example, the feedback generators may be located entirely above the sole, elsewhere within the cavity 108 of the footwear apparatus, elsewhere on the footwear apparatus or combinations thereof.

Further, any appropriate type of actuator may be incorporated into the feedback generators. In the illustrated example, the actuator is a motor driven gear that is shaped and positioned to move the pin towards the user's foot. In other examples, the actuator is a solenoid, a linear actuator, a magnetic actuator, a hydraulic actuator, a pneumatic actuator, a gear assembly, a spring assembly, an electric assembly, a gear assembly, another type of actuator or combinations thereof.

Also, any appropriate type of mechanism may be used to provide the stimulus to the user's foot. In the illustrated example, the impingement heads 122, 124 are configured to make contact with the user's feet, which provides a haptic communication to the user that his or her activity technique is off. However, other types of haptic communications may be provided. In one example, the distal end of the pins contacts the user's feet without having impingement heads. In other examples, a ball, a rod, a bead, an arm, another type of structure or combinations thereof is moved towards the user's feet. In yet other examples, the user's foot is pinched, stabbed, pricked, squeezed, bumped, knocked, thumped, twisted, grabbed or otherwise physically contacted with a structure of the feedback generator. In other examples, an electrical haptic communication is generated by the feedback generator to correct his or her technique associated with the user's activity. Such an electrical haptic communication can provide a localized shock to the user to motivate the user to change at least one aspect of the user's technique.

While the examples above have been described with specific reference to motivating the user to avoid heel striking during a running activity, the feedback generators can be used to motivate the user to change any appropriate aspect of the user's technique across multiple types of activities. For example, if the user's stride frequency and/or stride length is too short, the feedback generators may provide a stimulus to the user to motivate the user to lengthen his or her stride or to decrease his or her stride frequency. In other examples, the feedback generators may be used to cause the user to shorten his or her stride or to increase his or her stride frequency.

In some examples, the measurements collected by the sensors can be sent to the remote device for at least some processing. For example, such information may be sent to a mobile device carried by the user. In such a manner, the processor of the mobile device may be used to interpret the measurements from the sensors in the footwear apparatus. By using a processor in a remote device, the footwear apparatus does not have to incorporate a processor. Thus, the power to operate a processor does not have to be local to the footwear apparatus. Further, the footwear apparatus is freed from having to store local memory for processing the measurements. However, in some examples, the footwear apparatus includes a processor, a power source, memory or combinations thereof to interpret the sensor's recordings. In some examples, the sensors and the feedback generators are configured to use as little power as possible for operation. In such an example, the data from the sensors may be sent to a remote processor in raw form and the remote processor may send the instructions to the feedback generator to activate. In other examples, the instructions to activate the feedback generators are processed locally.

The recorded measurements can be stored temporarily in memory in the footwear apparatus 100 and then be transmitted to a remote device. Such memory may include a buffer, a cache, another type of short term memory or combinations thereof. In such examples, the temporarily stored measurements may be sent to the remote device on a periodic basis that allows the measurements to be obtained by the remote device in real time or near real time. For example, a transmitter of the footwear apparatus 100 may send the stored data to the remote device at one second intervals, sub-second intervals, microsecond intervals, other types of intervals, real time, near real time or combinations thereof. In other examples, the measurements may be continuously transmitted to the remote device. Likewise, instructions from the remote device may be sent to the feedback generators at one second intervals, sub-second intervals, microsecond intervals, other types of intervals, real time or combinations thereof.

In some examples, the measurements from the sensors are analyzed in real time and instructions to the feedback generators are sent in real time. In other examples, the measurements from the sensors are analyzed after a predetermine amount of data is collected or time has passed so that there is a sufficient amount of data to process to determine the patterns associated with the user's technique. Instructions based on such collective data may be sent to the feedback generators with an instruction to provide the haptic communication to the user for a predetermined time period. The user's technique may be further analyzed to determine whether the user's technique improved or otherwise changed since the last stimulus from the feedback generators. In such examples, the instructions to the feedback generator may be modified for a second predetermined time period. Such changes to the instructions may include changes to which of the feedback generators are to activate, the strength of the haptic communication to the user, the timing of the haptic communications, other changes, other commands or combinations thereof.

In examples where local power is used, the footwear apparatus may include a battery. In other examples, a power harvesting mechanism may be used to harness the kinetic energy of the user's activity for powering the sensors and/or feedback generator. Such a power harvesting mechanism may include a slideable magnet that moves through at least one turn of a coil based on the user's activity. In other examples, a temperature differentials between the shoe and the user's foot, between the inside the cavity 108 and outside of the footwear apparatus, between the underside of the footwear's sole (where heat is generated due to friction between the footwear apparatus and the ground) and another part of the footwear apparatus, between other locations of the footwear apparatus or combinations thereof can be used to drive a thermoelectric effect based energy harvesting devices, such as a Seeback device. Such a thermoelectric device may use the differences in thermal energy from the various parts of the shoe to operate the sensors, the feedback generators, other components of the footwear apparatus or combinations.

Figure 3:
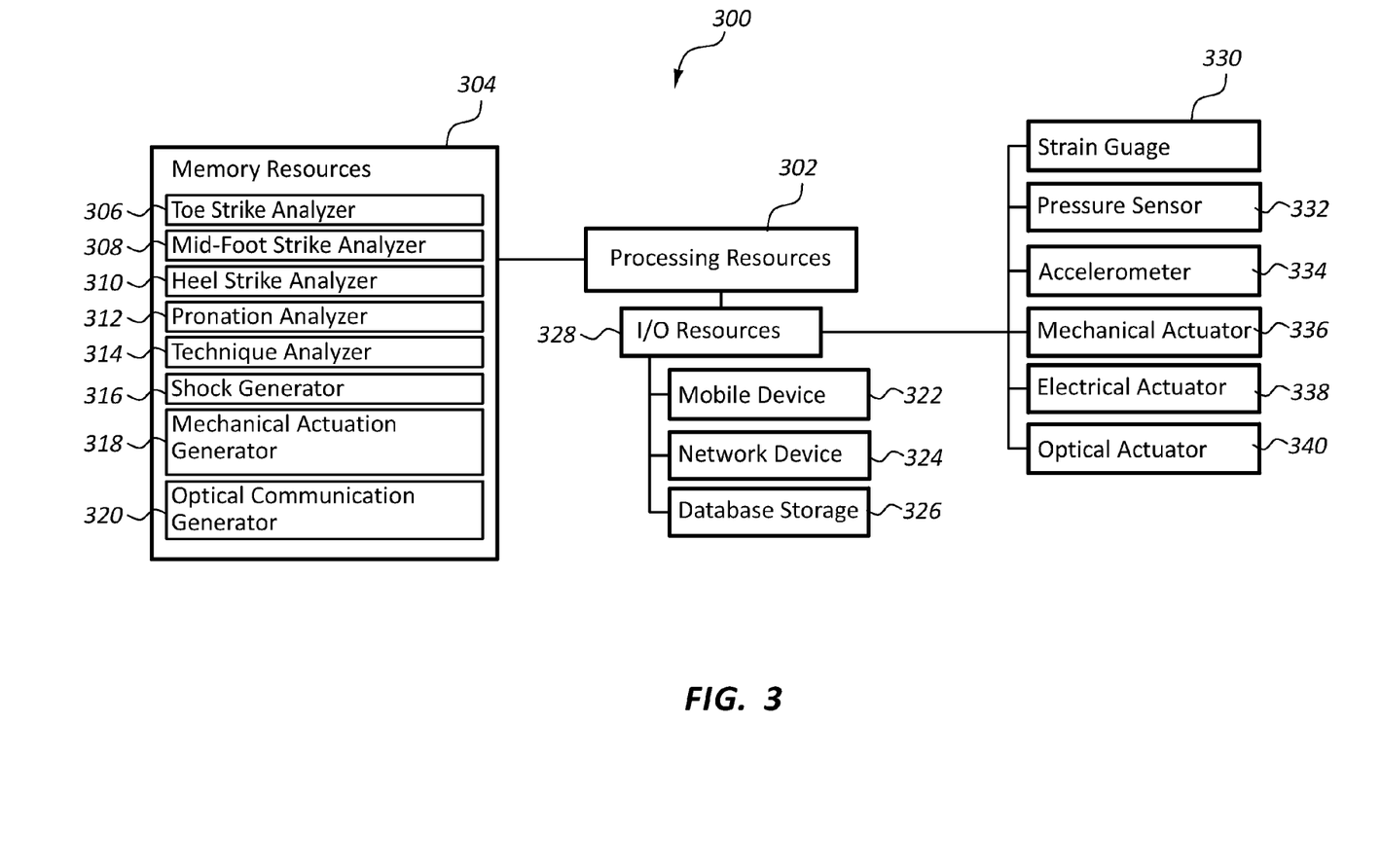
FIG. 3 illustrates a diagram of an example of a feedback system in accordance with the present disclosure.

FIG. 3 illustrates a block diagram of an example of a feedback system 300 in accordance with the present disclosure. The feedback system 300 may include a combination of hardware and programmed instructions for executing the functions of the system 300. In this example, the system 300 includes processing resources 302 that are in communication with memory resources 304. Processing resources 302 include at least one processor and other resources used to process the programmed instructions. The memory resources 304 represent generally any memory capable of storing data such as programmed instructions or data structures used by the system 300. The programmed instructions shown stored in the memory resources 304 include a toe strike analyzer 306, a mid-foot strike analyzer 308, a heel strike analyzer 310, a pronation analyzer 312, a technique analyzer 314, a shock generator 316, a mechanical actuation generator 318 and an optical communication generator 320. While this example has been described with reference to specific programmed instructions, any appropriate combination of programmed instructions may be included. For example, some of the programmed instructions described above may or may not be incorporated into each embodiment of the invention. Further, additional programmed instructions may be incorporated into other examples in accordance with the principles described in the present invention.

Further, the processing resources 302 may be in communication with user information and/or workout environment information that may be stored in the memory resources 304 locally or off site. For example, the processing resources 302 may be in communication with a remote device that stores the user information or workout environment information. Such a remote device may be a mobile device 322, a network device 324, a database storage device 326, another type of device or combinations thereof. In some examples, the system communicates with other remote device through the mobile device 322 which relays communications between the system 300 and the remote devices. In other examples, the mobile device 322 has access to information about the user and/or workout environment. In some cases, the remote device collects general information about the user or specific information relating to the user's activity. In one such example, the measurements collected by the sensors may be sent to the remote device indicating how long the user performed the activity, the stride length, the stride frequency, the heel strike rate, the toe strike rate, the mid-foot strike rate, other aspects of the user's technique, other types of information about the activity or combinations thereof. This information may be used by programmed instructions for executing their functions. The remote device may execute a program that can provide useful information to the system 300. An example of a program that may be compatible with the principles described herein includes the iFit program which is available through www.ifit.com and administered through ICON Health and Fitness, Inc. located in Logan, Utah, U.S.A. An example of a program that may be compatible with the principles described in this disclosure are described in U.S. Pat. No. 7,980,996 issued to Paul Hickman. U.S. Pat. No. 7,980,996 is herein incorporated by reference for all that it discloses. In some examples, the user information accessible through the remote device includes the user's age, gender, body composition, height, weight, health conditions, other types of information or combinations thereof. Further, the workout environment information that may be accessible to the remote device may include humidity data, temperature data, elevation data, atmospheric pressure data, sunlight exposure data, other types of environmental data or combinations thereof.

The processing resources 302, memory resources 304 and remote devices may communicate over any appropriate network and/or protocol through the input/output resources 328. In some examples, the input/output resources 328 includes a transceiver for wired and/or wireless communications. For example, these devices may be capable of communicating using the ZigBee protocol, Z-Wave protocol, BlueTooth protocol, Wi-Fi protocol, Global System for Mobile Communications (GSM) standard, another standard or combinations thereof. In other examples, the user can directly input some information into the system 300 through a digital input mechanism, a mechanical input mechanism, another type of mechanism or combinations thereof. The input/output resources 328 may be in communication with the sensors and feedback generators. In some specific examples, the input/output resources 328 may be in communication with a strain gauge 330, a pressure sensor 332, an accelerometer 334, a mechanical actuator 336, an electrical actuator 338, an optical actuator 340, another type of sensor, another type of actuator, another type of feedback generator, another type of device or combinations thereof.

The memory resources 304 include a computer readable storage medium that contains computer readable program code to cause tasks to be executed by the processing resources 302. The computer readable storage medium may be a tangible and/or non-transitory storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic based memory, other types of memory or combinations thereof.

The toe strike analyzer 306 represents programmed instructions that, when executed, cause the processing resources 302 to analyze sensor measurements that indicate whether the user's toe is striking the ground during the activity. The mid-foot strike analyzer 308 represents programmed instructions that, when executed, cause the processing resources 302 to analyze sensor measurements that indicate whether the user's mid-foot is striking the ground during the activity. The heel strike analyzer 310 represents programmed instructions that, when executed, cause the processing resources 302 to analyze sensor measurements that indicate whether the user's heel is striking the ground during the activity.

The pronation analyzer 312 represents programmed instructions that, when executed, cause the processing resources 302 to analyze sensor measurements that indicate whether the user's feet are pronating during the activity. Pronation determinations may include whether the user's foot has an inward or outward rolling motion during the activity. Pronation may be quantified in terms of degrees or be based on where the user's foot pushes off of the ground.

The technique analyzer 314 represents programmed instructions that, when executed, cause the processing resources 302 to analyze multiple sensor measurements to determine the user's technique. In response to determining the user's technique, instructions may be sent to the feedback generators to provide feedback to the user about his or her technique and to provide motivation for the user to change at least one aspect of the user's technique.

The shock generator 316 represents programmed instructions that, when executed, cause the processing resources 302 to generate a shock to provide feedback about the user's technique and to motivate the user to change at least one aspect of his or her technique. Such a shock may be an electrical shock that is produced with an electronic mechanism configured to release electrical energy into the user's foot. The amount of electrical energy released into the user's foot is below a threshold that is harmful to the user, but still high enough that the user can feel the energy release.

The mechanical actuation generator 318 represents programmed instructions that, when executed, cause the processing resources 302 to generate physical contact on the user's foot to provide feedback about the user's technique and to motivate the user to change at least one aspect of his or her technique. Such a physical contact may include moving a structure into the user's foot. The geometry and/or force used to move the structure may cause the user discomfort in the region of the foot where the desired change is to take place. For example, if the user is walking on the forward right side of his or her foot, the physical contact may be imposed on the forward right side of the user's foot, thus, motivating the user to avoid walking on the forward right side of the foot.

The optical communication generator 320 represents programmed instructions that, when executed, cause the processing resources 302 to send an optical message that is capable of being seen by the user to provide feedback about the user's technique and to motivate the user to change at least one aspect of his or her technique. Such optical communication may include light emitting diodes (LEDs) that are incorporated on the outside of the footwear apparatus. The user can view as the LEDs illuminate and make decisions about how to modify his or her technique. For example, the illumination of a single LED may indicate heel striking, while the illumination of two LEDs indicates pronation. Likewise, various other patterns of LED illuminations may indicate other aspects of the user's technique.

Further, the memory resources 304 may be part of an installation package. In response to installing the installation package, the programmed instructions of the memory resources 304 may be downloaded from the installation package's source, such as a portable medium, a server, a remote network location, another location or combinations thereof. Portable memory media that are compatible with the principles described herein include DVDs, CDs, flash memory, portable disks, magnetic disks, optical disks, other forms of portable memory or combinations thereof. In other examples, the program instructions are already installed. Here, the memory resources 304 can include integrated memory such as a hard drive, a solid state hard drive or the like.

In some examples, the processing resources 302 and the memory resources 304 are located within footwear apparatus, an accessory of the footwear apparatus, a mobile device carried by the user, another type of device or combinations thereof. The memory resources 304 may be part of any of these device's main memory, caches, registers, non-volatile memory or elsewhere in their memory hierarchy. Alternatively, the memory resources 304 may be in communication with the processing resources 302 over a network. Further, data structures, such as libraries or databases containing user and/or workout information, may be accessed from a remote location over a network connection while the programmed instructions are located locally. Thus, the system 300 may be implemented with footwear apparatus 100, a user device, a mobile device, a phone, an electronic tablet, a wearable computing device, a head mounted device, a server, a collection of servers, a networked device, a watch or combinations thereof. Such an implementation may occur through input mechanisms, such as push buttons, touch screen buttons, voice commands, dials, levers, other types of input mechanisms or combinations thereof. Any appropriate type of wearable device may include, but are not limited to glasses, arm bands, leg bands, torso bands, head bands, chest straps, wrist watches, belts, earrings, nose rings, other types of rings, necklaces, garment integrated devices, other types of devices or combinations thereof.

The feedback system 300 of FIG. 3 may be part of a general purpose computer. However, in alternative examples, the system 300 is part of an application specific integrated circuit.

Figure 4:
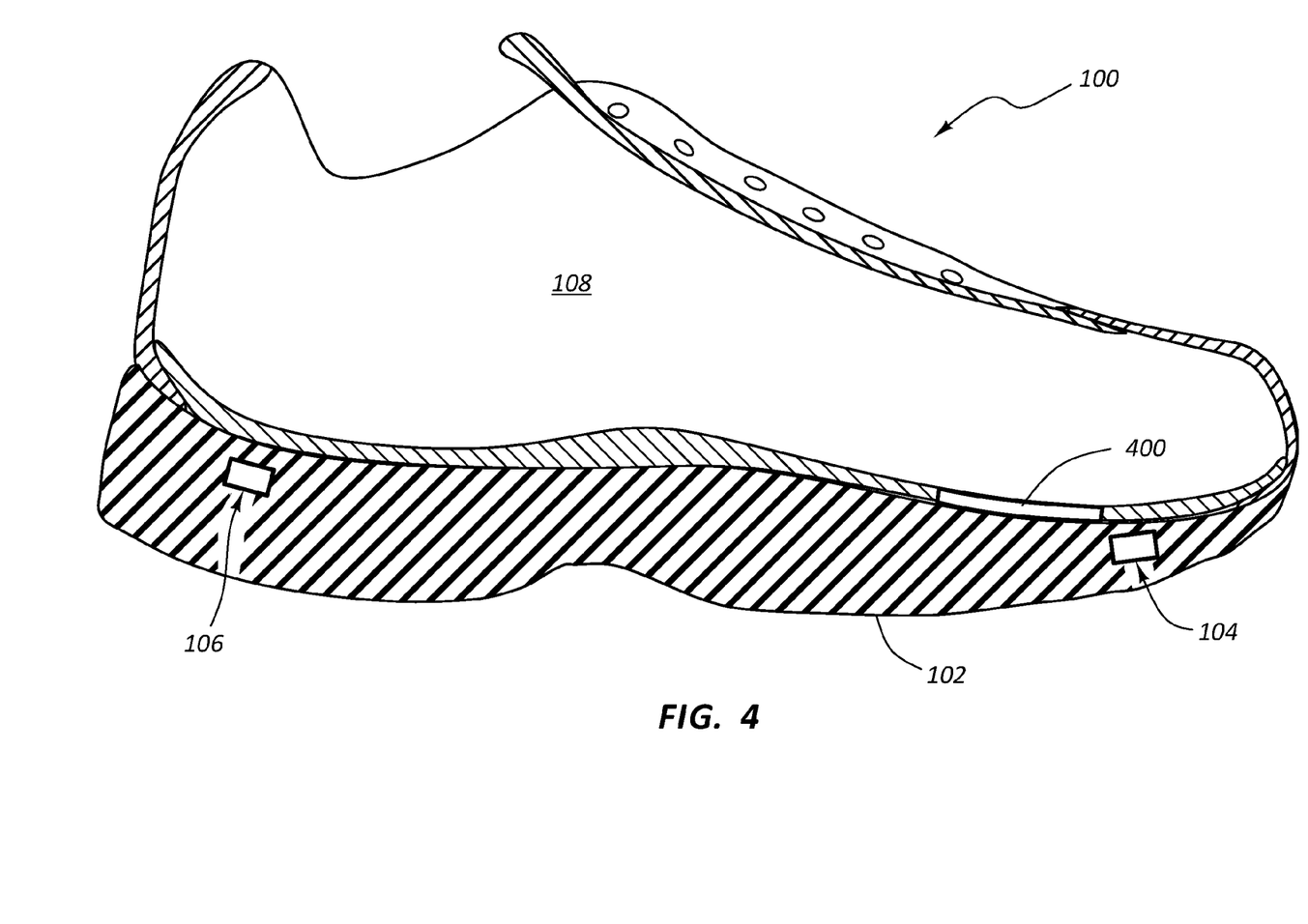
FIG. 4 illustrates a cross sectional view of an example of a footwear apparatus in accordance with the present disclosure.

FIG. 4 illustrates a cross sectional view of a footwear apparatus 100 in accordance with the present disclosure. In this example, the footwear apparatus 100 includes a front sensor 104 and a rear sensor 106 to record measurements that can be used to make determinations about the user's technique. In this example, an electrically conductive electrode 400 is disposed within the cavity 108 of the footwear apparatus 100. The electrode 400 may be in communication with an electrical power source, such as a battery, an energy harvesting mechanism, another type of power source or combinations thereof. An electrical shock may be applied to the user's foot through the electrode to provide feedback to the user about his or her technique. While the illustrated example depicts a single electrode in a single location of the footwear apparatus, any number of electrodes may be disposed within the footwear apparatus to apply electrical shocks to other locations of the foot. Such electrodes may be positioned to apply electrical shocks to the underside of the foot, the side of the foot, the top of the foot, the front of the foot, the rear of the foot, another side of the foot or combinations thereof.

Figure 5:
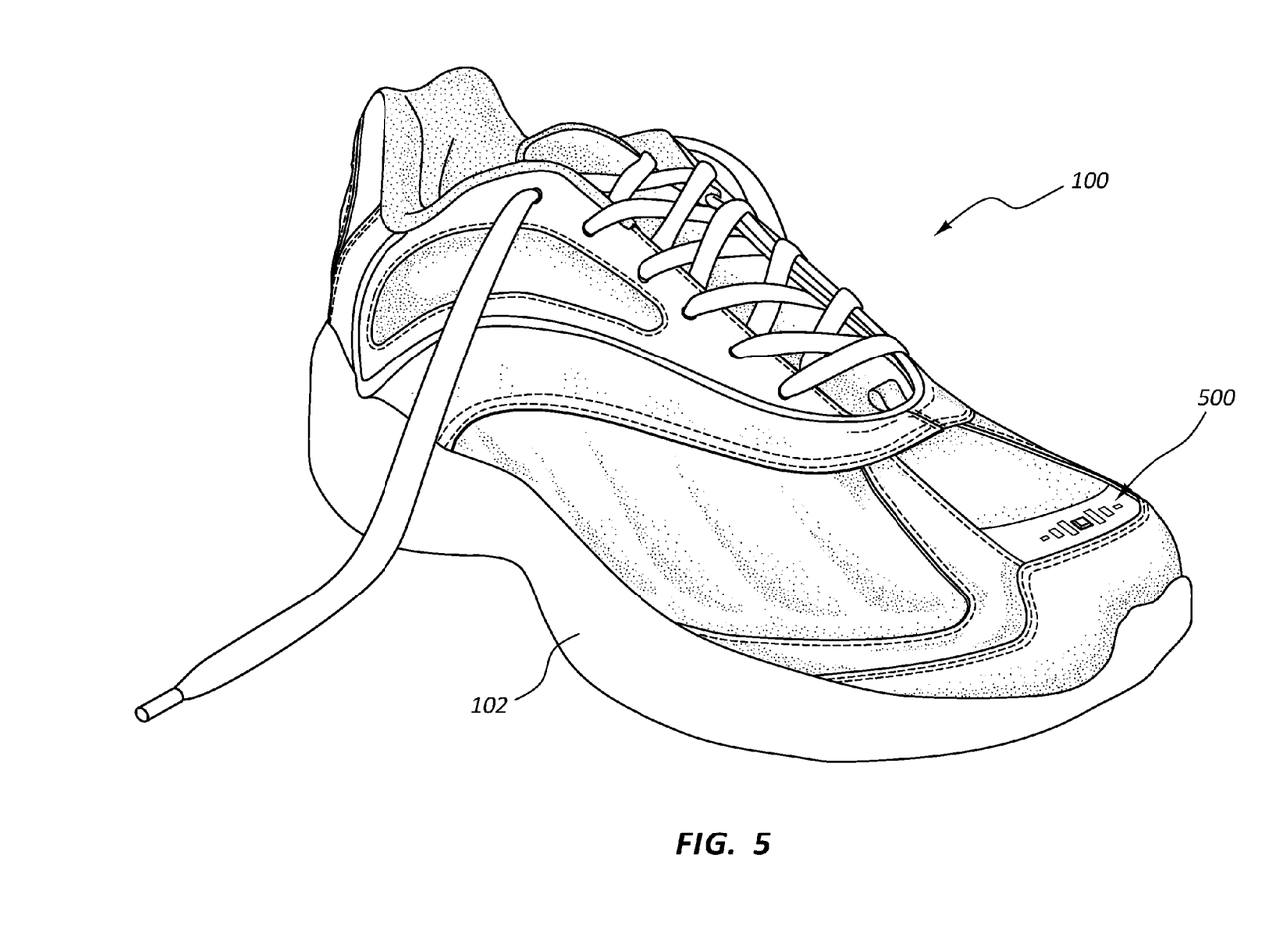
FIG. 5 illustrates a perspective diagram of an example of a footwear apparatus in accordance with the present disclosure.

FIG. 5 illustrates a perspective diagram of an example of a footwear apparatus 100 in accordance with the present disclosure. In this example, a set of LEDs 500 is incorporated into the outside of the footwear apparatus 100. The location of the LEDs 500 is such that the LEDs 500 are visible to the user when the LEDs 500 illuminate.

The illumination of multiple lights may indicate that the user's technique includes certain conditions, such as a high degree of pronation, heel striking, other conditions or combinations thereof. As the user performs his or her activity, the user can view the LEDs on the footwear apparatus 100 to view feedback about his or her technique. Based on the feedback, the user may adjust his or her technique. After changing his or her technique, the user may view the LEDs 500 again to determine if the same technique issues persist even after making adjustments. If a new issue arises or the same issues persist, the user can repeat the process of viewing the illumination of the LEDs 500 and making adjustments accordingly.

While the above examples have been described with reference to the certain feedback generators providing physical contact with the user's foot to provide feedback and motivation to alter the user's technique, it should be understood that such physical contact may occur through a user's sock or other clothing inside the footwear's cavity 108. For example, the impingement heads 122, 124 may press up against the sock, compress the sock and push against the foot such that the user can feel the impingement heads 122, 124 through the sock. Further, the impingement heads 122, 124 may push with an appropriate amount of force to cause the user to feel discomfort through his or her sock. The principles may be applied in other situations where different types of structure are arranged to make physical contact with the foot. Likewise, in those embodiments where an electrical shock is applied to a portion of the user's foot, the electrical shock may be applied through the user's sock or other clothing.

While the examples above have been described with reference to the sensors, feedback generators and other components being incorporated into various parts of the footwear apparatus, it should be understood that such parts of the footwear apparatus 100 may include an insert that is removably placed within the cavity 108 of the footwear apparatus 100. For example, an existing shoe may be retrofitted by placing a shoe insert into the cavity 108 where the insert includes at least one sensor and at least one feedback generator.

While the examples above have been described with reference to the footwear apparatus being a shoe, any appropriate type of footwear apparatus may be used in accordance with the principle described herein. For example, a non-exhaustive list of footwear apparatus types include shoes, running shoes, walking shows, cleats, boots, slippers, ballet slippers, downhill ski boots, cross country ski boots, sandals, therapeutic types of footwear, ice skates, in-line skates, hiking boots, other types of footwear apparatus or combinations thereof.

INDUSTRIAL APPLICABILITY

In general, the invention disclosed herein may provide a user with a footwear apparatus that includes a feedback mechanism for determining whether the user's technique associated with an activity can be improved. In some examples, the feedback includes haptic communication. In other examples, the feedback includes optical communication. The haptic communication may include electrical shocks or physical contact from structures that are moved relatively closer to the user's foot, ankle, leg, toe, heel or combinations thereof.

In one example, sensors and feedback generators are incorporated into the soles of the footwear apparatus. The sensors are pressure sensors, accelerometers, strain gauges, other types of sensors or combinations thereof. The measurements recorded with the sensors can be analyzed to make determinations about the user's technique. Based on the interpretation of the sensor's recorded information, the instructions can be sent to the feedback generators to cause a structure to make contact with the user's foot. In some circumstances, the contact causes physical discomfort to the user to provide additional motivation to the user to correct his or her technique. In other examples, other types of haptic feedback may include electrical shocks. In yet other examples, a visual mechanism may provide the feedback to the user, such as through at least one illuminating element incorporated into the footwear apparatus 100 that is visible to the user during the execution of the technique. In that manner, the user can view during the activity whether his or her technique can be improved.

What is claimed is:

1. A footwear apparatus comprising:
    a sensor in the footwear apparatus positioned to monitor an activity technique of a user when the footwear apparatus is joined with a foot of the user, and
    a feedback generator arranged to produce a haptic communication to the user in response to detecting a pattern in the activity technique, the haptic communication arranged to cause at least some discomfort to the user, wherein the pattern includes a pronation element.

2. The footwear apparatus of claim 1, wherein the pattern is undesirable for the activity technique.

3. The footwear apparatus of claim 1, wherein the footwear apparatus comprises a shoe.

4. The footwear apparatus of claim 1, wherein the haptic communication is an electric shock.

5. The footwear apparatus of claim 1, wherein the haptic communication includes a mechanical mechanism arranged to come into contact with the foot.

6. The footwear apparatus of claim 1, wherein the feedback generator comprises an actuator capable of moving an impingement head into contact with the foot.

7. The footwear apparatus of claim 6, wherein the impingement head is one of multiple impingement heads.

8. The footwear apparatus of claim 7, wherein the multiple impingement heads are distributed throughout a support member of the footwear apparatus in a heel region of the support member, a toe region of the support member, a mid-foot region of the support member or combinations thereof.

9. The footwear apparatus of claim 6, wherein the impingement head is connected to an impingement body at least partially submerged in a thickness of a support member of the footwear apparatus, the impingement head having a longitudinal axis, the impingement body having a longitudinal axis, the impingement head having a larger lateral dimension than a lateral dimension of the impingement body.

10. The footwear apparatus of claim 9, wherein the impingement head is positioned such that the foot lands on the impingement head when the impingement head is caused to protrude beyond a foot engagement surface of the support member such that the impingement head one or more of pinches, stabs, and pricks the foot of the user.

11. The footwear apparatus of claim 1, wherein the pattern includes a toe striking element.

12. The footwear apparatus of claim 1, wherein the pattern includes a heel striking element.

13. The footwear apparatus of claim 1, wherein the pattern includes a mid-foot striking element.

14. A footwear apparatus, comprising:
a sensor in the footwear apparatus positioned in one or more of an inner arch portion and an outer arch portion of the footwear apparatus to monitor pronation of a foot of a user during an activity technique of the user when the footwear apparatus is joined with the foot of the user; and
a feedback generator arranged to produce a haptic communication to the user in response to detecting whether the user's foot has an inward or outward rolling motion;
wherein the haptic communication includes a mechanical mechanism arranged to come into contact with at least a portion of the inner arch portion or the outer arch portion of the foot.

15. The footwear apparatus of claim 14, wherein the haptic communication is executed with one or more impingement heads.

16. The footwear apparatus of claim 15, wherein the impingement heads are distributed throughout the inner arch portion of the user's foot and the outer arch portion of the user's foot on a support member of the footwear apparatus in a heel region of the support member, a toe region of the support member, a mid-foot region of the support member or combinations thereof.

17. The footwear apparatus of claim 15, wherein the impingement heads are connected to impingement bodies at least partially submerged in a thickness of a support member of the footwear apparatus.

18. A footwear apparatus, comprising:
a sensor in the footwear apparatus positioned in one or more of an inner arch portion and an outer arch portion of the footwear apparatus to monitor an activity technique of the user when the footwear apparatus is joined with the foot of the user;
a feedback generator arranged to produce a haptic communication to the user in response to detecting whether the user's foot has an inward or outward rolling motion, the haptic communication arranged to cause at least some discomfort to the user;
the haptic communication includes a mechanical mechanism arranged to come into contact with at least a portion of one or more of the inner arch portion and the outer arch portion of the foot;
the haptic communication is executed with impingement heads;
the impingement heads are distributed throughout a support member of the footwear apparatus in a heel region of the support member, a toe region of the support member, a mid-foot region of the support member or combinations thereof;
the impingement heads are connected to impingement bodies at least partially submerged in a thickness of the support member of the footwear apparatus, the impingement head having a longitudinal axis, the impingement body having a longitudinal axis, the impingement head having a larger lateral dimension than a lateral dimension of the impingement body; and
the impingement heads are positioned such that the foot lands on the impingement heads when the impingement heads are caused to protrude beyond foot engagement surface of the support member such that the impingement head one or more of pinches, stabs, and pricks the foot of the user.

19. The footwear apparatus of claim 6, wherein the impingement head is shaped to cause discomfort when the impingement head contacts the foot of the user.

20. The footwear apparatus of claim 15, wherein at least one of the one or more impingement heads are connected to an impingement body at least partially submerged in a thickness of a support member of the footwear apparatus, the impingement head having a longitudinal axis, the impingement body having a longitudinal axis, the impingement head having a larger lateral dimension than a lateral dimension of the impingement body.

* * * * *